United States Patent [19]

Chan

[11] 4,407,817
[45] Oct. 4, 1983

[54] FUNGICIDAL 3-(N-ACYL-N-ARYLAMINO)- AND 3-(N-THIONOACYL-N-ARYLAMINO)-GAMMA-BUTYROLACTONES AND GAMMA-THIOBUTYROLACTONES

[75] Inventor: David C. K. Chan, Petaluma, Calif.

[73] Assignee: Chevron Research Company, San Francisco, Calif.

[21] Appl. No.: 369,713

[22] Filed: Apr. 19, 1982

Related U.S. Application Data

[63] Continuation-in-part of Ser. No. 228,048, Jan. 26, 1981, abandoned, Continuation of Ser. No. 44,740, Jan. 1, 1979.

[51] Int. Cl.³ .................... A01N 43/08; A01N 43/10; C07D 307/32; C07D 333/36

[52] U.S. Cl. .................... 424/275; 424/274; 424/279; 548/518; 548/550; 549/60; 549/63; 549/321

[58] Field of Search .................. 424/275, 279; 549/60, 549/63, 321

[56] References Cited

U.S. PATENT DOCUMENTS

| | | | |
|---|---|---|---|
| 4,012,519 | 3/1977 | Chan | 424/274 |
| 4,032,657 | 6/1977 | Moser | 424/309 |
| 4,093,738 | 6/1978 | Hubele | 424/309 |
| 4,107,323 | 8/1978 | Chan | 424/279 |
| 4,241,078 | 12/1980 | Chan | 424/275 |

*Primary Examiner*—Richard Raymond
*Attorney, Agent, or Firm*—D. A. Newell; T. G. De Jonghe; L. S. Squires

[57] ABSTRACT

3-(N-acyl-N-arylamino) and 3-(N-thionoacyl-N-arylamino)-gamma-butyrolactones and thiobutyrolactones have fungicidal activity.

13 Claims, No Drawings

FUNGICIDAL 3-(N-ACYL-N-ARYLAMINO)- AND 3-(N-THIONOACYL-N-ARYLAMINO)-GAMMA-BUTYROLACTONES AND GAMMA-THIOBUTYROLACTONES

CROSS-REFERENCE TO RELATED APPLICATIONS

This application is a continuation-in-part of U.S. application Ser. No. 228,048, filed Jan. 26, 1981, now abandoned, which is a continuation of U.S. application Ser. No. 44,740, pending filed June 1, 1979, the disclosures of both of which applications are hereby incorporated by reference.

BACKGROUND OF THE INVENTION

U.S. Pat. No. 3,933,860, issued Jan. 26, 1976, U.S. Pat. No. 4,012,519, issued Mar. 15, 1977, U.S. Pat. No. 4,107,323, issued Aug. 15, 1978, U.S. Pat. No. 4,141,989, issued Feb. 27, 1979, and U.S. Pat. No. 4,241,078, issued Dec. 23, 1980, all to David Cheong King Chan, disclose the use of a large class of 3-(N-acyl-N-arylamino) lactones and 3-(N-acyl-N-arylamino) lactams and thiolactones as fungicides.

U.S. Pat. No. 4,034,108, issued July 5, 1977, to H. Moser, and U.S. Pat. No. 4,015,648, issued May 24, 1977 to H. Moser, disclose the use of N-(methoxycarbonylethyl)-N-haloacetylanilines as preventive and curative fungicides.

German Patent Publication Nos. 2,643,403 and 2,643,445, published Apr. 7, 1977, disclose the use of N-(alkylthiocarbonylethyl)acetanilides for controlling fungi, particularly those of the class Phycomycetes.

Netherlands Patent Publication No. 152,849, published Apr. 15, 1977, discloses the use of N-(alkoxymethyl)acetanilides as fungicides.

Belgian Pat. No. 867,556, published Nov. 27, 1978, discloses 3-N-(cyclopropylcarbonyl-N-arylamino)-gamma-butyrolactones.

Belgian Pat. No. 863,615, published Aug. 3, 1978, discloses fungicidal 3-(N-acyl-N-arylamino)-gamma-butyrolactones.

Recently it has been found that subsequent generations of the fungi producing grape downy mildew disease which have been treated with one of the fungicides commonly used to control this disease (i.e., N-methoxyacetyl-N-(1-methoxycarbonylethyl)-2,6-dimethylaniline) are appearing to exhibit resistance to this fungicide. Further, it appears that this resistance also increases the resistance of such fungi to a number of the newer aniline derivative fungicides. If this resistance becomes widespread, it will present considerable problems to the control of this disease.

SUMMARY OF THE INVENTION

It has now been found that 3-(N-acyl-N-arylamino)- and 3-(N-thionoacyl-N-arylamino)-gamma-butyrolactones and butyrothiolactones are effective for the control of fungi, especially for downy mildew fungal infection caused by fungal species of the Peronosporaceae family and late blight fungal infection caused by *Phytophthora infestans*. In particular, novel fungicidal compounds have been found wherein the N-acyl group is alkenyl carbonyl and alkenyl oxide carbonyl. Novel fungicidal N-thionoacyl compounds have also been found. Some of the compounds of the invention are effective both as protectant fungicides, i.e., they prevent or protect against fungal infections, and as eradicant fungicides, i.e., they eliminate and cure established infections. The compounds of the invention are especially preferred for the control of grape downy mildew. Certain of these compounds further exhibit substantial activity against the resistance strains of fungi discussed above.

DESCRIPTION OF THE INVENTION

The compounds of the invention are represented by the formula

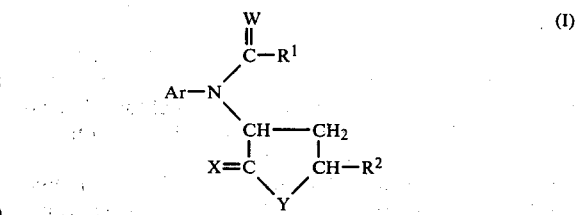

wherein Ar is phenyl, naphthyl, or phenyl or naphthyl substituted with 1 to 4 of the same or different substituents selected from fluoro, chloro, bromo, alkyl of 1 to 4 carbon atoms or alkoxy of 1 to 4 carbon atoms; $R^1$ is alkenyl of 2 to 6 carbon atoms, alkenyl oxide of 2 to 6 carbon atoms or alkenyl of 2 to 6 carbons atoms substituted by halogen or alkoxy of 1 to 4 carbon atoms; $R^2$ is hydrogen, chloro, bromo, alkyl of 1 to 6 carbon atoms, phenyl or phenyl substituted with 1 to 2 of the same or different substituents selected from fluoro, chloro, bromo and alkyl of 1 to 6 carbon atoms; Y is O, S or —NH—; W is O or S, and X is O or S; with the proviso that when W is S, $R^1$ is, in addition to the groups recited above, hydroxymethyl, halomethyl of 1 to 3 of the same or different halogens selected from fluoro, chloro or bromo, alkoxyalkyl of 2 to 6 carbon atoms, alkylthioalkyl of 2 to 6 carbon atoms, phenylthioalkyl of 7 to 10 carbon atoms, phenoxyalkyl of 7 to 10 carbon atoms, phenylthioalkyl or phenoxyalkyl of 7 to 10 carbon atoms substituted on the phenyl ring with 1 to 2 of the same or different substituents selected from fluoro, chloro, bromo, alkyl of 1 to 4 carbon atoms or alkoxy of 1 to 4 carbon atoms, cycloalkyl or 3 to 6 carbon atoms, cycloalkyl of 3 to 6 carbon atoms substituted with 1 to 4 of the same or different substituents selected from alkyl of 1 to 4 carbon atoms, fluoro, chloro, bromo, hydroxy or alkoxy of 1 to 4 carbon atoms.

Representative substituted-phenyl groups which Ar may represent are 2-fluorophenyl, 2,4-dichlorophenyl, 3,5-dibromophenyl, 4-methylphenyl, 2,6-diethylphenyl, 4-methoxyphenyl, 4-nitrophenyl, 2,6-dimethyl-4-chlorophenyl, 2,3,6-trimethylphenyl, 2,3,5,6-tetramethylphenyl. Preferred substituted-phenyl Ar groups are phenyl substituted with 1 to 2 of the same or different substituents selected from chloro, bromo, alkyl of 1 to 4 carbon atoms or alkoxy of 1 to 4 carbon atoms. Most preferred substituted-phenyl Ar groups are 2,6-dialkylphenyl, especially 2,6-dimethylphenyl.

Representative substituted-naphthyl Ar groups are 1-naphthyl, 2-naphthyl, 1-methyl-2-naphthyl, 4-methyl-2-naphthyl, 4-methyl-1-naphthyl, 2-chloro-1-naphthyl, 2-methoxy-1-naphthyl, 2,4-dimethyl-1-naphthyl and 2,7-dimethyl-1-naphthyl. Preferred substituted naphthyl Ar groups are 2-alkyl-1-naphthyl groups, especially 2-methyl-1-naphthyl.

Representative halomethyl groups which $R^1$ may represent include fluoromethyl, chloromethyl, bromomethyl, dichloromethyl, tribromomethyl and fluorodichloromethyl. The preferred halomethyl R¹ group is chloromethyl.

Representative alkoxyalkyl R¹ groups are methoxymethyl, ethoxymethyl, isopropoxymethyl and n-pentoxymethyl. The preferred alkoxyalkyl R¹ group is methoxymethyl.

Representative alkylthioalkyl R¹ groups are methylthiomethyl, n-propylthiomethyl and n-pentylthiomethyl.

Representative cycloalkyl of R¹ groups are cyclopropyl, cyclobutyl, cyclopentyl, cyclohexyl, and 4-methylcyclohexyl.

Representative substituted-phenylthioalkyl and substituted-phenoxyalkyl R¹ groups are 4-chlorophenylthiomethyl, 4-methylphenoxymethyl, 2,4-dichlorophenoxymethyl, 3,5-dimethylphenylthiomethyl and 2-chloro-4-methylphenoxymethyl.

Representative alkenyl R¹ groups are vinyl, 2-methylvinyl, 2,2-dimethylvinyl, 1-methylvinyl, allyl, isopropenyl, butenyl, 3-methoxyprop-1-en-1-yl, 3-chloroprop-1-en-1-yl. The preferred alkenyl groups are vinyl, 2-methylvinyl, 1-propenyl and 2,2-dimethylvinyl.

Representative R¹ alkenyl oxide groups are oxiranyl, 1-methoxiran-1-yl, 2,2-dimethyloxiran-1-yl, 2-methyloxiran-1-yl.

Representative alkyl R² groups are methyl, ethyl, isopropyl and n-hexyl. Representative substituted-phenyl R² groups are 2-chlorophenyl, 2,4-dichlorphenyl, 4-methylphenyl and 2,3-dimethylphenyl.

Preferably Ar is phenyl substituted with 1 to 2 of the same or different substituents selected from fluoro, chloro, bromo or alkyl of 1 to 2 carbon atoms, or 2-alkyl-1-naphthyl. The most preferred Ar groups are 2,6-dimethylphenyl or 2-methyl-1-naphthyl.

Preferably R¹ is vinyl, 2-methylvinyl, 2,2-dimethylvinyl, alkoxymethyl of 1 to 6 carbon atoms, chloromethyl or bromomethyl. Most preferably R¹ is vinyl, allyl, 2-methylvinyl, 1,2-epoxypropyl, methoxymethyl or chloromethyl.

Preferably X and W are both oxygen. When W is sulfur, R¹ is preferably methoxymethyl.

Preferably R² is hydrogen or methyl.

A preferred class of N-phenylamino and N-substituted phenylaminolactones is that represented by the formula (II)

(II)

wherein R¹ is alkenyl of 2 to 6 carbon atoms or alkenyl oxide of 2 to 6 carbon atoms, R² is hydrogen or methyl, and R⁴ and R⁵ individually are methyl or ethyl, and Y is O or S. Particularly preferred compounds of formula (II) are those wherein R¹ is vinyl, 2-methylvinyl, 1,2-epoxypropyl or 2,2-dimethylvinyl, R² is hydrogen and R⁴ and R⁵ are methyl.

The R¹ is propenyl compounds of formula II wherein R⁴ and R⁵ are each methyl and R² is hydrogen, have excellent activity against *Phytophthora infestans;* i.e., the fungus which causes Tomato Late Blight. Also, based on recent fungicide agar studies with N-methoxyacetyl- N—(1-methoxycarbonylethyl)-2,6-dimethylaniline resistant mutant strains of *Pythium ultimum* or *Pythium vexans* it was found that the compound of Formula II wherein R¹ is —CH=CHCH₃, R² is H, R⁴ is —CH₃, R⁵ is —CH₃ and Y is O exhibit fungicidal activity against these resistant strains of fungi.

The 3-(N-thionoacyl-N-arylamino) lactones and thiolactones of the invention may be represented by the formula (III)

wherein Ar is phenyl, naphthyl or substituted phenyl or naphthyl as previously defined, and R¹, X, Y and R² have the same significance as previously defined. A preferred class of 3-(N-thionoacyl-N-arylamino) lactones is that represented by the formula (IV)

wherein R¹ is alkoxyalkyl of 2 to 6 carbon atoms, R² is hydrogen or methyl, and R⁴ and R⁵ individually are methyl or ethyl. Preferred compounds of Formula (IV) are those wherein R¹ is methoxymethyl, R² is hydrogen, and R⁴ and R⁵ are methyl.

Representative compounds of the Formula (I) are:
3-(N-acryloyl-N-2,6-dimethylphenylamino)-gamma butyrolactone, 3-(N-3-methylcrotonyl-N-2,6-dimethylphenylamino)-gamma-butyrolactone,
3-(N-crotonyl-N-2,6-dimethylphenylamino)-gamma-butyrolactones,
3-(N-acryloyl-N-2,6-dimethylphenylamino)-gamma-thiobutyrolactone,
3-(N-2-methylacryloyl-N-2-methyl-6-ethylphenylamino)-gamma-butyrolactone,
3-(N-3-methyl-2,3-epoxy-butanoyl-N-2,6-dimethylphenylamino)-gamma-butyrolactone,
3-(N-2-methyl-2,3-epoxy-propanoyl-N-2,6-dimethylphenylamino)-gamma-butyrolactone,
3-(N-methoxythionoacetyl-N-2,6-dimethylphenylamino)-gamma-butyrolactone,
3-(N-methoxythionoacetyl-N-2,6-dimethylphenylamino)-gamma-thiobutyrolactone.

The lactone and thiolactone compounds of the invention may be prepared by methods disclosed in my copending application, Ser. No. 13,856, filed Feb. 22, 1979, the disclosure of which is incorporated by reference, by alkylating an aniline (VIII) with alpha-halo-gamma-butyrolactones or alpha-halo-gamma-thiobutyrolactones (IX) and subsequently acylating the alpha-(N-arylamino)-gamma-butyrolactones or thiobutyrolactones (X) with an acyl halide (XI) to give the 3-(N-acyl-N-arylamino)-gamma-butyrolactones or thiobutyrolactones product (IA), as depicted by the following equations:

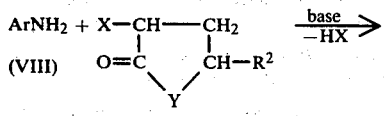

(IX)

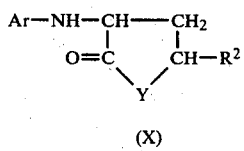

(X)

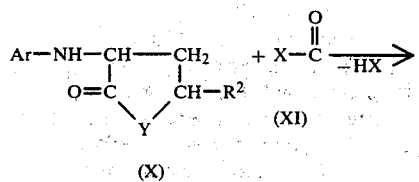

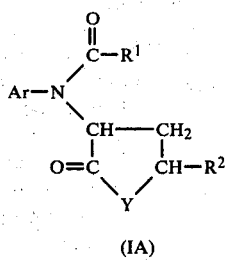

(IA)

wherein Ar, $R^1$, $R^2$ and Y have the same significance as previously defined, and X is chloro or bromo.

The alkylation reaction (1) is conducted in the presence of a base. Suitable bases are inorganic alkali metal carbonates such as sodium carbonates or potassium carbonate or organic amines such as trialkylamines, e.g., triethylamine, or pyridine compounds, e.g., pyridine or 2,6-dimethylpyridine. Generally, substantially equimolar amounts of reactants (VIII) and (IX) and the base are employed. In one modification of the reaction, a molar excess of the aniline reactant (VIII) is used as the base, and no additional base is employed. The reaction is conducted in inert organic solvents, e.g., apolar diprotic solvents such as dimethylformamide and acetonitrile and aromatic hydrocarbons such as benzene and toluene, at reaction temperatures varying from 25° C. to 150° C., preferably from 50° C. to 150° C. Water may be employed as a cosolvent. The reaction pressure may be atmospheric, subatmospheric or superatmospheric. However, for convenience of conducting the reaction, the pressure is generally atmospheric. The reaction time will, of course, vary depending upon the reactants and the reaction temperature. Generally, the reaction time is from 0.25 to 24 hours. The product (X) is generally purified by conventional procedures, e.g., extraction, distillation or crystallization, before use in the acylation reaction (2).

Preferred alkylation reaction conditions are given in more detail in the commonly assigned application of Richard N. Reynolds, Jr., entitled "Alkylation of Aniline with a Lactone in the Presence of Water", Ser. No. 847,503, filed Nov. 1, 1977.

The acylation reaction (2) is conducted by conventional procedures. The reactants (X) and (XI) are generally contacted in substantially equimolar amounts in an inert organic solvent at a temperature of 0° to 100° C. Suitable inert organic solvents include ethyl acetate, methylene dichloride, dimethoxyethane, benzene, etc. The product is isolated and purified by conventional procedures such as extraction, distillation, chromatography, crystallization, etc.

When preparing a butyrolactone product (compounds of Formula (I) wherein W, X and Y=O), an organic amine such as a trialkylamine or a pyridine compound may be employed as an acid acceptor. However, when preparing a butyrothiolactone product (compounds of Formula (I) wherein W and X=O and Y=S), an organic amine should not be employed.

Preferred acylation reaction conditions are given in more detail in the commonly assigned application of Richard N. Reynolds, Jr., Stephen D. Ziman and David C. K. Chan, entitled "Acylation of Lactone-Substituted Aniline Compound in the Absence of an Acid Acceptor", Ser. No. 847,504, filed Nov. 1, 1977.

The compounds of Formula (IA) wherein $R^1$ is alkylthioalkyl, phenylthioalkyl or substituted-phenylthioalkyl may be prepared from the corresponding compound wherein $R^1$ is haloalkyl by reacting the corresponding haloalkyl compound with an alkali metal mercaptide by conventional procedures as depicted in the following equation (3) in the case where $R^1$ is alkylthiomethyl:

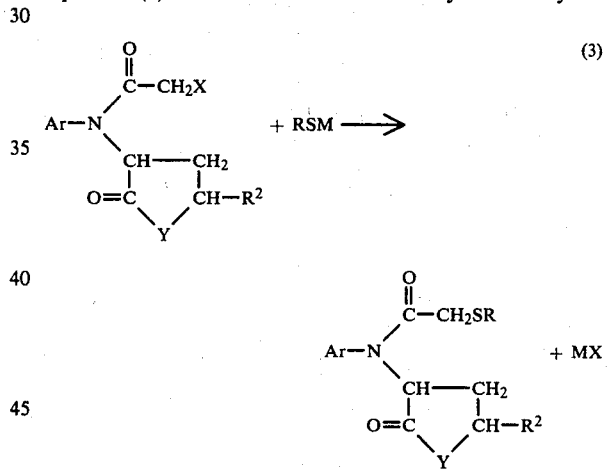

wherein Ar, $R^2$, X and Y are as previously defined, M is alkali metal, R is alkyl, phenyl or substituted phenyl. In reaction (3), Y preferably is oxygen.

The compounds of Formula (IA) wherein $R^1$ is hydroxymethyl and Y is oxygen may be prepared by treatment of the corresponding compound wherein $R^1$ is halomethyl with an inorganic alkali metal hydroxide, such as aqueous sodium hydroxide. The compounds of Formula (IA) wherein $R^1$ is hydroxymethyl and Y is oxygen or sulfur may be prepared by hydrolysis of the corresponding compound wherein $R^1$ is alkanoylmethyl.

Compounds of the Formula (IA) wherein $R^1$ is alkenyl oxide are prepared by oxidizing the corresponding compound wherein $R^1$ is alkenyl with an oxidizing agent such as 3-chloroperbenzoic acid, in the presence of an inorganic base, such as potassium acid phosphate.

The compounds of Formula (IA) wherein $R^2$ is chloro or bromo are generally prepared by chlorinating or brominating the corresponding compound wherein $R^2$ is hydrogen with a chlorinating or brominating agent such as N-bromosuccinimide or N-chlorosuccinimide by conventional procedures, as depicted in the following equation (4):

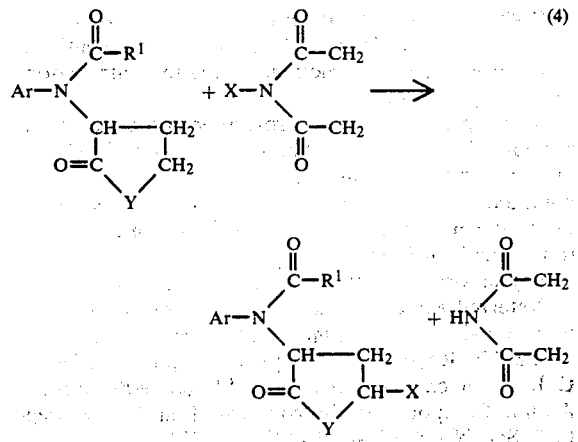

wherein Ar, $R^1$, Y and X are as previously defined.

The 3-(N-thionoacyl-N-arylamino) butyrolactones and thiobutyrolactones are prepared from the corresponding 3-(N-acyl-N-arylamino) butyrolactones and thiobutyrolactones of the Formula (II) according to the following scheme:

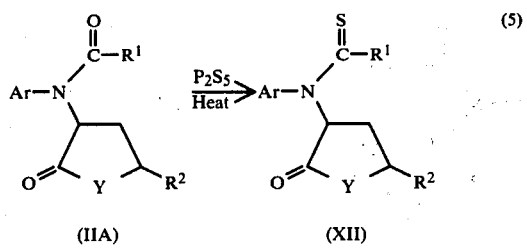

The reaction (5) is carried out at the reflux temperature of the solvent, preferably xylene, with molar ratio of (IIA) to phosphorous pentasulfide of about 4:1, in the presence of a trace of a base, such as pyridine. The product (XII) may be isolated by conventional chromatography.

UTILITY

The compounds of the invention are useful for controlling fungi, particularly plant fungal infections. However, some fungicidal compositions of the invention may be more fungicidally active than others against particular fungi. For example, the activity of the preferred compounds of the invention is highly specific for certain fungal diseases such as downy mildews, e.g., *Plasmopara viticola* (grapes) and *Peronospora parasitica* (cabbage and collard), late blights, e.g., *Phytophthora infestans* (tomatoes and potatoes), and crown and root rots, e.g., Phytophthora.

The compounds of the invention are particularly useful fungicides because they cure established fungal infections. This permits economical use of the fungicides of the invention, because they need not be applied to plants unless fungal infection actually occurs. Thus, a preventative program of applying fungicides against potential fungal infection is not necessary.

When used as fungicides, the compounds of the invention are applied in fungicidally effective amounts to fungi and/or their habitats, such as vegetative hosts and nonvegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitatig dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, wettable, inorganic diluents. Typical wetting, dispersing or emulsifying agents include, for example: the aryl and alkylaryl sulfonates and their sodium salts, alkylamide sulfonates, including fatty methyl taurides; alkylaryl polyether alcohols, sulfated higher alcohols and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLES

The preparation and fungicidal activity of the compounds of the invention is illustrated by the following examples.

Example 1—Preparation of 3-(N-methoxyacetyl-N-2,6-dimethylphenylamino)-gamma-thiobutyrolactone A solution of 1.46 g (0.0135 mol) methoxyacetyl chloride in 10 ml dichloromethane was added dropwise to a refluxing solution of 3 g (0.0135 mol) 3-(N-2,6-dimethylphenylamino)-gamma-thiobutyrolactone in 200 ml toluene. The reaction mixture was heated at reflux for 3 hours and evaporated to give a solid. The solid was recrystallized from a 10:1:10 solvent mixture of ether:benzene:hexane to give 1.8 g of the product, as a tan solid, m.p. 86°–87° C. The infrared spectrum of the product showed two strong carbonyl absorption bands at 5.85 microns and 6.03 microns.

Example 2—Preparation of 3-(N-acetoxyacetyl-N-2,6-dimethylphenylamino)-gamma-butyrolactone A 13.7-g (0.1-mol) sample of acetoxyacetyl chloride was added dropwise to a solution of 20.5 g (0.1 mol) N-2,6-dimethylphenylamino-gamma-butyrolactone and 7.9 g (0.1 mol) pyridine in 150 ml benzene. After completion of the addition, the reaction mixture was stirred at about 25° C. for 4 hours, then washed with water, dried over magnesium sulfate and evaporated under reduced pressure to give an oily residue. The residue was crystallized from ethyl ether/hexane to give 27.3 g of product, m.p. 90°–91° C.

3-(N-cyclopropylcarbonyl-N-2,6-dimethylphenylamino)-gamma-butyrolactone can be made in an analogous manner using cyclopropylcarbonyl chloride and N-2,6-dimethylphenylamino-gamma-butyrolactone as starting materials.

Example 3—Preparation of N-hydroxyacetyl-N-2,6-dimethylphenylamino-gamma-butyrolactone A solution of 50 g (0.18 mol) 3-(N-chloracetyl-N-2,6-dimethylphenylamino)-gamma-butyrolactone, 14.5 g (0.36 mol) sodium hydroxide dissolved in 50 ml water, and 450 ml dimethoxyethane was stirred at about 25° C. for 16 hours. The resulting reaction mixture was filtered, diluted with 500 ml dichloromethane. Hydrogen chloride gas was bubbled into the reaction mixture for 1 hour. The reaction mixture was filtered, dried over magnesium sulfate, and evaporated under reduced pressure. The residue was washed with 10% ethyl ether/90% hexane, filtered and air-dried to give 36.5 g of the product as a white crystalline solid, m.p. 173°–174° C.

Example 4—Preparation of N-ethoxyacetyl-N-2,6-dimethylphenylamino-gamma-butyrolactone A 6.2-g (0.05-mol) sample of ethoxyacetyl chloride was added dropwise to a refluxing solution of 10.3 (0.05 mol) 3-(N-2,6-dimethylphenylamino)-gamma-butyrolactone in 150 ml toluene. The reaction mixture was then heated under reflux for 2 hours. After cooling, the reaction mixture was washed with water, washed with saturated sodium bicarbonate solution, washed with water, dried over magnesium sulfate and evaporated to give 11.2 g of 3-(N-ethoxyacetyl-N-2,6-dimethylphenylamino)-gamma-butyrolactone, m.p. 73°–75° C.

Example 5—Preparation of N-methylthioacetyl-N-2,6-dimethylphenylamino)-gamma-butyrolactone A 22-g (0.3-mol) sample of sodium methylmercaptide was added in small portions to a solution of 25.3 g (0.08 mol) N-bromoacetyl-N-2,6-dimethylphenylamino)-gamma-butyrolactone, m.p. 116°–117° C., in 200 ml dimethyl sulfoxide. A mild exotherm ensued. The reaction mixture was allowed to stir at about 25° C. for about 16 hours. The reaction mixture was then heated to about 150° C. under reduced water aspirator pressure to remove a portion of the dimethyl sulfoxide solvent. The residue was diluted with water and the aqueous layer separated. The organic portion was dissolved in 350 ml dichloromethane, washed with water, dried over magnesium sulfate and evaporated under reduced pressure to give an oil. The oil was chromatographed through a silica gel column (20% acetone/80% petroleum ether solution) to give the product (11 g), which after crystallization from ethyl ether/acetone melted at 77°–78° C.

Example 6—Preparation of 3-(N-methoxyacetyl-N-2-methylnapth-1-ylamino)-gamma-butyrolactone A 2.4 g (0.022 mol) sample of methoxyacetyl chloride was added dropwise to a solution of 5.5 g (0.022 mol) 3-(N-2-methylnaphth-1-ylamino)-gamma-butyrolactone and 1.7 g (0.022 mol) pyridine in 100 ml dichloromethane. The reaction mixture was stirred one hour at about 25° C. and then heated under reflux for 6 hours. After cooling overnight, the reaction mixture was washed successively with water, saturated sodium bicarbonate solution, water, dried over magnesium sulfate and evaporated under reduced pressure. The residue was chromatographed through a silica gel column. Elution with 25% acetone/75% petroleum ether gave 4.3 g of the product, m.p. 42°–46° C.

Example 7—Preparation of 3-(N-methoxythionoacetyl-N-2,6-dimethylphenylamino)-gamma-butyrolactone A slurry of phosphorus pentasulfide (6.0 gm) in 300 ml xylene was heated under a Dean Stark water separator to azeotropically remove any water present.

After cooling to 100° C. pyridine (2 ml) was added followed by 3-(N-methoxyacetyl-N-2,6-dimethylphenylamino)-gamma-butyrolactone (33.3 g). The stirred slurry was heated at 150°. After about 45 minutes, the phosphorus pentasulfide dissolved and the mixture was kept at 150° over a weekend.

The mixture was diluted with an equal volume of methylene chloride and washed with saturated sodium bicarbonate (200 ml), water (200 ml) and dried (MgSO$_4$).

The solution was filtered and the filtrate was stripped in vacuo to yield a dark oil which was chromatographed in silica gel (300 g) by elution with petroleum ether, 80% petroleum ether in ethyl ether, 70% petroleum ether in ethyl ether, 60% petroleum ether in ethyl ether, 40% petroleum ether in ethyl ether and 25% petroleum ether in ethyl ether.

The oil isolated from the petroleum ether: ethyl ether elutions were dissolved in methylene chloride and treated with charcoal and MgSO$_4$, filtered and stripped to yield the title product as an oil (1.8 gm). The product is reported as compound 10 in Table B.

Example 8—Preparation of 3-(N-crotonyl-N-2, 6-dimethylphenylamino)-gamma-butyrolactone Crotonic acid (6 g) and thionyl chloride (12 g) were refluxed for one hour and the excess thionyl chloride was removed in vacuo. 3-(N-2,6-dimethylphenylamino)-gamma-butyrolactone (14 g) was added with 150 ml toluene and refluxed for 2 hours.

The mixture was washed with water, saturated sodium bicarbonate, dried (MgSO$_4$), filtered and stripped of solvent. The product was chromatographed on 260 gm silica gel; elution with acetone/ether/petroleum ether to yield 3.1 g of the title product, m.p. 122°–123° C. The product is reported as compound 3 in Table A.

Example 9—Preparation of 3-(N-3-methyl-2,3-epoxybutanoyl-N-2,6-dimethyl-phenylamino)-gamma-butyrolactone 3-(N-3-methyl-crotonyl-N-2,6-dimethyl-phenylamino)-gamma-butyrolactone (A) was prepared as in Example 8 using 3-methyl-crotonic acid as a starting material. Product A (9 g), 3-chloro-perbenzoic acid (6 g) and KH$_2$PO$_4$ (4.7 g) in 75 ml dichloromethane were refluxed for 48 hours.

The mixture was washed with water, dried (MgSO$_4$), stripped. The residue was crystallized in ether/hexane to yield 5.4 g of the title product, m.p. 100°–104° C. The product is reported as Compound 7 in Table A.

Example 10—Mycelial Inhibition

Compound 2 of the present invention was evaluated for fungicidal effectiveness by means of a mycelial inhibition test. This test is designed to measure the fungitoxic activity of fungicidal chemicals in terms of their degree of inhibition of mycelium growth. Compound 2 was dissolved in acetone to 500 ppm concentration. Paper strips were inoculated with *Pythium ultimum* mycelium growth by covering the paper with a potato dextrose broth culture of mycelial suspension. The inoculated papers were then placed on potato dextrose agar plates and sprayed by means of a micro sprayer with the fungicidal solution. The treated paper strips were incubated at 25° C. and data is taken after 24 hours. Fungicidal activities are measured by a zone of inhibited mycelial growth from the center of the paper strip. The effectiveness of Compound 2 tested for fungicidal activity is 100% in terms of percent inhibition relative to Difolatan.

Example 11—Tomato Late Blight

Compounds of the invention are tested for the preventative control of the Tomato Late Blight organism *Phytophthora infetans*. Five- to six-week-old tomato (cultivar Bonny Best) seedlings were used. The tomato plants were sprayed with a 250-ppm suspension of the test compound in acetone, water and a small amount of a non-ionic emulsifier. The sprayed plants were then inoculated one day later with the organisms, placed in an environmental chamber and incubated at 66°–68° F. and 100% relative humidity for at least 16 hours. Following the incubation, the plants were maintained in a greenhouse at 60–80% relative humidity for approximately 7 days. The percent disease control provided by a given test compound was based on the percent disease reduction relative to untreated check plants. The results are tabulated in Table I. In Table I, the test concentration is 250 ppm unless otherwise indicated by the figures in parentheses.

Example 12—Celery Late Blight

The celery late blight tests were conducted using celery (Utah) plants 11 weeks old. The celery late blight orgaism was *Septoria apii*. The celery plants were sprayed with solutions of the candidate toxicant mixed with acetone, water and a nonionic emulsifier. The plants were then inoculated with the organism and placed in an environmental chamber and incubated at 66°–68° F. in 100% relative humidity for an extended period of time (approximately 48 hours). Following the incubation the plants were allowed to dry and then were maintained at a 60–80% relative humidity for approximately 14 days. The percent disease control provided by a given candidate toxicant is based on the percent disease reduction relative to untreated check plants. The results are reported in Table I.

Example 13—Grape Downy Mildew Control

The compounds of the invention were tested for the control of the grape downy mildew organism *Plasmopara viticola*. Detached leaves, between 70 and 85 mm in diameter, of 7-week-old *Vitis vinifera* cultivar Emperor grape seedlings were used as hosts. The leaves were sprayed with a solution of the test compound in acetone. The sprayed laves were dried, inoculated with a spore suspension of the organism, placed in a humid environmental chamber and incubated at 18°–22° C. and about 100% relative humidity. Seven to nine days after inoculation, the amount of disease control was determined. The percent disease control provided by a given test compound was based on the percent disease reduction relative to untreated check plants. The results are tabulated in Table I.

Example 14—Tomato Early Blight

Compounds of the invention were tested for the control of the Tomato Early Blight organism, *Alternaria solani conidia*. Tomato (variety Bonny Best) seedlings of 6 to 7 weeks old were used. The tomato plants were sprayed with a 250-ppm solution of the test compound in an acetone-and-water solution containing a small amount of a nonionic emulsifier. The sprayed plants were inoculated one day later with the organism, dried and maintained at 60–80% relative humidity for about 12 days. Percent disease control was based on the percent disease development on untreated check plants.

The compounds were tested and the results are tabulated in Table I.

TABLE A

Compounds of the Formula

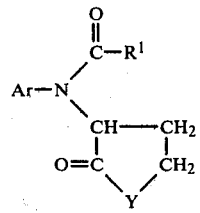

| Compound No. | Ar | Y | R¹ | m.p. °C. | C Calc. | C Found | H Calc. | H Found | N Calc. | N Found |
|---|---|---|---|---|---|---|---|---|---|---|
| 1 | 2,6-$(CH_3)_2\phi$ | O | $CH=CH_2$ | 142-3 | 69.48 | 68.7 | 6.61 | 6.77 | 5.40 | 5.42 |
| 2 | " | O | $CH=C(CH_3)_2$ | 86-7 | 71.06 | 71.39 | 7.37 | 7.67 | 4.88 | 4.96 |
| 3 | " | O | $CH=CHCH_3$ | 122-3 | 70.31 | 69.38 | 7.01 | 6.99 | 5.12 | 5.16 |
| 4 | " | S | $CH=CH_2$ | 101-2 | 65.43 | 62.56 | 6.22 | 6.23 | 5.09 | 4.93 |
| 5 | " | O | $C(CH_3)=CH_2$ | 115-23 | 70.31 | 68.5 | 7.01 | 6.99 | 5.12 | 5.17 |
| 6 | " | S | $CH=C(CH_3)_2$ | 123-4 | 67.29 | 68.25 | 6.98 | 7.2 | 4.62 | 4.86 |
| 7 | " | O | $CH\overset{O}{-\!\!\triangle\!\!-}C(CH_3)_2$ | 100-04 | 67.31 | 67.44 | 6.98 | 7.36 | 4.62 | 4.66 |
| 8 | " | O | $C(CH_3)\overset{O}{-\!\!\triangle\!\!-}CH_2$ | 109-10 | 66.42 | 68.3 | 6.62 | 7.05 | 4.84 | 5.02 |
| 11 | " | O | $CH\overset{O}{-\!\!\triangle\!\!-}CH-CH_3$ | 117-18 | 66.42 | 66.15 | 6.62 | 6.72 | 4.84 | 4.76 |
| 12 | " | S | $CH=CHCH_3$ | 117-122 | 66.4 | 68.17 | 6.62 | 6.98 | 4.84 | 5.0 |
| 13 | " | S | $CH_2CH=CH_2$ | 67-69 | 66.4 | 67.0 | 6.62 | 7.08 | 4.84 | 4.89 |
| 14 | " | O | $CH_2CH=CH_2$ | 84-87 | 70.31 | 70.65 | 7.01 | 7.42 | 5.13 | 5.26 |
| 15 | 2-methyl-naphth-1-yl | O | $CH=CHCH_3$ (rotamer A) | 166-172 | 73.77 | 72.13 | 6.19 | 6.36 | 4.53 | 4.45 |
| 16 | 2-methyl-naphth-1-yl | O | $CH=CHCH_3$ (rotamer B) | 104-111 | 73.77 | 74.53 | 6.19 | 6.65 | 4.53 | 4.92 |
| 17 | 2-methyl-naphth-1-yl (rotamer A) | O | $CH=CH_2$ | 158-176 | 73.2 | 73.35 | 5.80 | 5.79 | 4.74 | 4.43 |
| 18 | 2-methyl-naphth-1-yl (rotamer B) | O | $CH=CH_2$ | 177-179 | 73.2 | 71.32 | 5.80 | 5.92 | 4.74 | 4.53 |

TABLE B

Compounds of the Formula

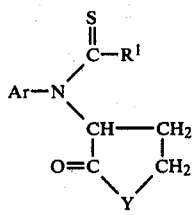

| Compound No. | Ar | Y | R¹ | m.p. °C. | C Calc. | C Found | H Calc. | H Found | N Calc. | N Found |
|---|---|---|---|---|---|---|---|---|---|---|
| 9 | 2,6-$(CH_3)_2\phi$ | O | $CH_2OCH_3$ | 85-6 | 61.41 | 66.17 | 6.53 | 6.82 | 4.77 | 5.35 |
| 10 | " | S | $CH_2OCH_3$ | Oil | 58.22 | 57.35 | 6.19 | 6.11 | 4.53 | 4.55 |

TABLE I

| No. | Grape Downy Mildew | Tomato Late Blight | Celery Late Blight | Tomato Early Blight |
|---|---|---|---|---|
| 1 | 89 | 0 | 65 | 7 |
| 2 | 54 | 0 | 23 | 0 |
| 3 | 100 | 100 | 33 | 29 |
| 4 | 100 | 57 | 94 | 29 |
| 5 | 18 | 23 | 23 | 18 |
| 6 | 54 | 13 | 57 | 8 |
| 7 | — | 14 | 11 | 11 |
| 8 | — | 0 | 50 | 11 |
| 9 | 100 | 98 | 37 | 0 |
| 10 | 100 | 99 | 50 | — |
| 11 | 100 | 71 | 23 | 0 |
| 12 | 100 | 84 | 36 | 0 |
| 13 | 100 | 96 | 44 | 0 |
| 14 | 100 | 96 | 44 | 0 |
| 15 | 100 | 89 | 11 | 0 |
| 16 | 100 | 84 | 37 | 0 |
| 17 | 100 | 37 | — | 0 |
| 18 | 83 | 0 | — | 0 |

% Control

Example 15

This example compares the fungitoxicity of 3-(N-crotonoyl-N-2,6-dimethylphenylamino)-gamma-butyrolactone, Formula II, $R^1$ is —CH=CHCH$_3$ of the present invention, against N-methoxyacetyl-N-(1-methoxycarbonyl-ethyl)-2,6-dimethylaniline resistant mutants of *Pythium ultimum* and/or *Pythium vexans* and also against the sensitive naturally occurring species of these fungi. The resistant mutants were obtained from the laboratory of L. V. Edgington of the University of Guelph.

This evaluation was conducted by preparing ethanol solutions of the test compound of the present invention and also of N-methoxyacetyl-N-(1-methoxycarbonyl-ethyl)-2,6-dimethylaniline as the "Control". One ml of the ethanol solutions was blended with 100 ml of melted V-8 juice agar. The medium was poured in plates and cooled. Plugs of agar plated mycelial cultures of the respective fungi were taken at the periphery with a #2 cork borer and placed upside down in the center of the treated agar plates. Measurements of surface growth (diameter in mm) were taken in 2 directions. These were averaged and the 8 mm diameter of inoculating plug was subtracted. The data was converted to dosage response curves on log probability graph paper and in turn to ED$_{50}$ values. Each treatment contained three replicates and was tested one or more times. Dosage response curves included 4 dosages of a compound.

The results of this evaluation are given in Table II hereinbelow. The ratio of ED$_{50}$-resistant to ED$_{50}$-sensitive is an indication of the degree that the compounds fungitoxicity will be affected by Control resistance developed by the fungi. The smaller the ratio, the more likely the compound is to overcome the Control resistance block. (The variation in the ratio between the two mutant species suggests that the developed resistance varies between the two mutants.)

The compound of the present invention exhibits very good effectiveness in controlling grape down mildew caused by non-mutant fungi and further as can be seen from Table III are less affected by mutant Control resistance than is the Control.

TABLE II

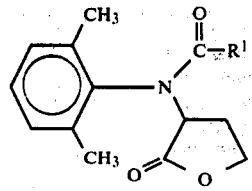

| | | Pythium ultimum | | | Pythium vexans | |
|---|---|---|---|---|---|---|
| $R^1$ | Sensitive (Naturally Occurring) ED$_{50}$ ppm | Resistant ED$_{50}$ ppm | ED$_{50}$ Ratio R/S | Sensitive (Naturally Occurring) ED$_{50}$ ppm | Resistant ED$_{50}$ ppm | ED$_{50}$ Ratio R/S |
| Control* | 0.036 | 940 | 26,000 | 0.075 | 635 | 8,467 |
| —CH=CHCH$_3$ | 0.07 | 240 | 3,430 | 1.0 | 140 | 140 |

*N—methoxyacetyl-N—(1-methoxycarbonylethyl)-2,6-dimethylaniline

Obviously, many modifications and variations of the invention described hereinbelow and below in the claims, can be made without departing from the essence and scope thereof.

What is claimed is:

1. A compound of the formula

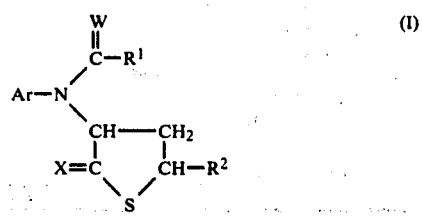

wherein Ar is phenyl, naphthyl, or phenyl or naphthyl substituted with 1 to 4 of the same or different substituents selected from fluoro, chloro, bromo, alkyl of 1 to 4 carbon atoms or alkoxy of 1 to 4 carbon atoms;

$R^1$ is alkenyl of 2 to 6 carbon atoms, optionally substituted by halogen or alkoxy of 1 to 4 carbon atoms, or alkenyl oxide of 2 to 6 carbon atoms;

$R^2$ is hydrogen, chloro, bromo, alkyl of 1 to 6 carbon atoms, phenyl or phenyl substituted with 1 to 2 of the same or different substituents selected from fluoro, chloro, bromo and alkyl of 1 to 6 carbon atoms;

W is O or S; and

X is O or S.

2. A compound according to claim 1 wherein $R^1$ is alkenyl of 2 to 6 carbon atoms.

3. A compound according to claim 1 wherein W and X are oxygen.

4. A compound according to claim 3 wherein Ar is 2,6-dialkylphenyl, and $R^2$ is hydrogen.

5. A method for the control of fungi which comprises contacting said fungi or their habitats with a fungicidally effective amount of a compound of the formula defined in claim 1.

6. A method for controlling the growth of *Phytophthora infestans* fungi which comprises applying to said fungi or their habitats a fungicidally effective amount of a compound of claim 1.

7. A method for controlling the growth of *Plasmopara viticola* fungi which comprises applying to said fungi or their habitats a fungicidally effective amount of a compound of claim 1.

8. A fungicidal composition comprising a biologically inert carrier and a fungicidally effective amount of a compound of claim 1.

9. The compound of claim 4 wherein Ar is 2,6-dimethylphenyl and $R^1$ is vinyl.

10. A compound selected from the group having the formula

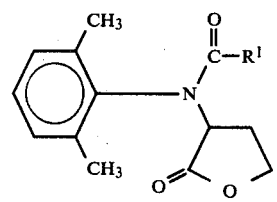

wherein $R^1$ is the group having the formula —CH=CH$_2$CH$_3$ or —CH$_2$CH=CH$_3$.

11. The compound of claim 10 wherein $R^1$ is the group —CH=CH$_2$CH$_3$.

12. A method for the control of fungi which comprises contacting said fungi or their habitats with a fungicidally effective amount of a compound of claim 10.

13. A fungicidal composition comprising a biologically inert carrier and a fungicidally effective amount of a compound of claim 10.

* * * * *